United States Patent [19]

Lueders et al.

[11] Patent Number: 4,861,513

[45] Date of Patent: Aug. 29, 1989

[54] PREPARATION OF SPECIFICALLY ADJUSTED POLYALCOHOL MIXTURES BASED ON SORBITOL

[75] Inventors: Harald Lueders, Recklinghausen; Hans-Josef Ratajczak; Ekkehard Wienhoefer, both of Marl, all of Fed. Rep. of Germany

[73] Assignee: Huels Aktiengesellschaft, Marl, Fed. Rep. of Germany

[21] Appl. No.: 106,507

[22] Filed: Oct. 9, 1987

[30] Foreign Application Priority Data

Feb. 4, 1987 [DE] Fed. Rep. of Germany ....... 3703257

[51] Int. Cl.$^4$ ................................................. C09G 3/00
[52] U.S. Cl. ........................... 252/182.24; 252/182.25; 252/182.27
[58] Field of Search ....................... 252/182.25, 182.27, 252/182.24

[56] References Cited

U.S. PATENT DOCUMENTS

| | | | |
|---|---|---|---|
| 3,640,920 | 2/1972 | Cear | 252/182 |
| 3,737,391 | 6/1973 | Feltzin et al. | 252/182 |
| 3,833,526 | 9/1974 | Cear et al. | 252/182 |
| 4,297,290 | 10/1981 | Stockburger | 260/410.6 |
| 4,380,502 | 4/1983 | Müller et al. | 252/182 |

OTHER PUBLICATIONS

Shoemaker et al, "Experiments in Physical Chemistry", pp. 419–421, McGraw-Hill Book Co. Inc. (1962) New York.

Perry et al, "Chemical Engineers' Handbook", 5th Ed., p. 22-2, 47, 49, McGraw-Hill Book Co. (1973) New York.

*Primary Examiner*—Edward A. Miller
*Attorney, Agent, or Firm*—Oblon, Spivak, McClelland, Maier & Neustadt

[57] ABSTRACT

A polyalcohol mixture is produced by heating dehydrating a reaction mixture comprising D-sorbitol, L-sorbitol or a mixture thereof in the presence of an acid catalyst. The reaction progress is followed by measuring the optical rotation of the reaction mixture during the reaction. The reaction is stopped when the optical rotation value of the reaction mixture corresponds to the optical rotation value of the desired polyalcohol mixture.

10 Claims, 2 Drawing Sheets

PREPARATION OF SPECIFICALLY ADJUSTED POLYALCOHOL MIXTURES BASED ON SORBITOL

BACKGROUND OF THE INVENTION

1. Field of the Invention

The invention relates to polyalcohol mixtures obtained by the dehydration of D-sorbitol, L-sorbitol or mixtures thereof. Specifically, the invention relates to a method of obtaining a specific polyalcohol mixture by monitoring the optical rotation of the dehydration reaction.

2. Discussion of the Background

Emulsifiers based on sorbitan esters, which demonstrate very specific hydrophilic and hydrophobic properties and can be completely synthesized on the basis of renewable raw materials are increasingly used in practice. It is known that the property profile of these esters is decisively influenced by the composition of the polyalcohol mixture on which they are based, for example, sorbitol, monoanhydrosorbitol (sorbitan), dianhydrosorbitol (isosorbide), etc. For this reason, there is interest in processes which make it possible to produce specifically adjusted polyalcohol mixtures based on sorbitol.

Various processes are known for producing anhydropolyls starling from D-sorbitol (see e.g. B. R. Barker, *J. Org. Chem.*, 35, 461 (1970), J. Feldmann et al., EP-OS 0 052 295 and DE-OS 30 14 626, Soltzberg et al., *J. Am. Chem. Soc.*, 68, 919, 927, 930 (1946) and S. Ropuszinski et al., *Prozed. Chem*, 48, 665 (1969)). In all these processes, water is split off intramolecularly, in the presence of an acid catalyst and at a raised temperature, and mixtures of anhydrous forms are always obtained. The polyalcohol mixture obtained by dehydration consists, for example, according to K. Bock et al. *(Acta Chem. Scand.,* 835, 441–449 (1981)), of 41.9% D-sorbitol, 49.0% 1,4-anhydro-D-sorbitol, 2.4% 3,6-anhydro-D-sorbitol, 3.7% 2,5-anhydro-L-iditol, 1.0% 2,5-anhydro-D-mannitol, and 2.1% 1,4:2,6-dianhydro-D-sorbitol.

As the reaction progresses, the concentration of dianhydrosorbitol increases, while that of sorbitol decreases.

Until now, all efforts to stop the dehydration at the stage of monoanhydrosorbitol, or to continue the reaction until exclusively dianhydrosorbitol is formed, have failed.

Defined polyalcohol mixtures can basically be produced by mixing the components. This procedure, however, presupposes cleaning and isolation of the components. But since only mixtures occur in all cases and separation is difficult, this method of procedure is extremely complicated and requires great effort.

A possibility of producing such mixtures in a targeted manner is proposed in DE-OS 30 41 626. According to this reference, the dehydration reaction time is selected in such a way that a certain hydroxyl number is reached. The process of G. J. Stockburger in U.S. Patent 4,297,290 provides for heating sorbitol in the presence of toluenesulfonic acid until an OH number of 1,195 has been attained in the reaction mixture, and subsequently carrying out esterification in the presence of sodium hydroxide. Determination of the OH number is known to be an experimental procedure which requires a lot of time. It is not suitable for directly following the progress of a reaction. Rather, it is only possible, in preliminary experiments, to determine the point in time at which a certain OH number will presumably be reached. A targeted quenching of the reaction is not possible in this way. A number of factors, such as, for example, temperature, pressure, stirring velocity, concentration ratios, nitrogen bubbling velocity, relative surface, batch size, water content and quality of the initial substances, significantly influence the reaction velocity. The process is therefore only reproducible under strictly identical conditions. These procedures are therefore not suitable for practical situations, where such parameters undergo contiual slight changes. Therefore, it is disclosed in DE-OS 30 41 626 that for each individual case, the optimum reaction time first has to be determined (c.f. column 6, line 59–65).

There have been efforts to determine the reaction progress directly by following the reaction parameters over time. E. Soltys et al., *Tulszcze, Srodki Piorace, Kosmet,* 13, 48 (1969), *Chem. Abstr.* 71, 124 831 (1969) describe such a method. The viscosity is used as a measure of the reaction progress. It is known, however, that the viscosity is significantly dependent on the concentration of the solvent, in this case water. But since the concentration of the water is specifically dependent on the factors which also influence the reaction velocity, this method is not suitable for following the progress of the reaction.

Fleche and Huchette follow the kinetics of the dehydration reaction using high-pressure liquid chromatography. This process can only be carried out discontinuously. Although it does yield fairly reliable values, it is technically complicated and requires a significant amount of time. It is therefore also undesirable for following the reaction on a technical scale (see Starch/Starke 38, 26–30 (1986)).

SUMMARY OF THE INVENTION

Accordingly, one object of the present invention is to provide a process for the dehydration of sorbitol and the monitoring of the dehydration reaction directly and immediately.

Another object of the invention is to provide a method of accurately producing a specific polyalcohol mixture.

A further object of the invention is to provide a process of monitoring the dehydration reaction progress which is economical and does not require great effort and yet yields reliable values.

These and other objects which will become apparent from the following specification have been achieved by the present process for the production of a polyalcohol mixture, which comprises the steps of:

(i) heating and dehydrating a reaction mixture comprising D-sorbitol, L-sorbitol or a mixture thereof in the presence of an acid catalyst;

(ii) measuring the optical rotation value of said reaction mixture during said heating and dehydrating step; and (iii) stopping said heating and dehydrating when said optical rotation value of said reaction mixture corresponds to the optical rotation value of said polyalcohol mixture.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
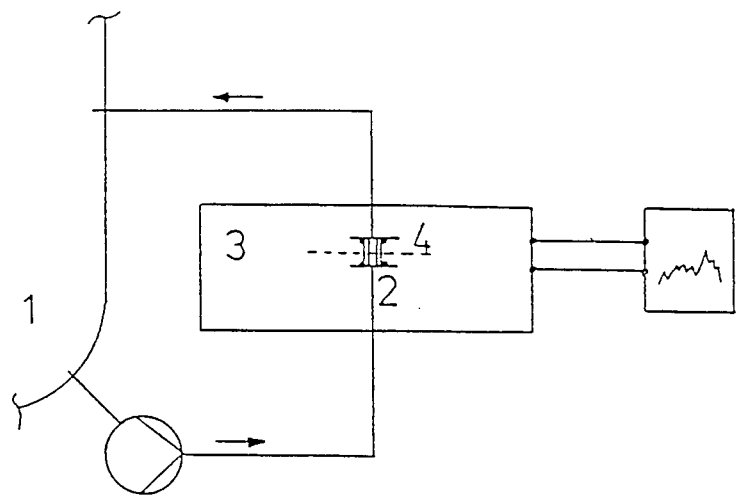
FIG. 1 illustrates an apparatus for the continuous measurement of the optical rotation value of the reaction mixture.

It has now been found that the optical rotation value is especially suitable for following the reaction progress. This is surprising, since dehydration of sorbitol is a complex reaction and a large number of intermediate and final reaction products are observed, each with different physical properties.

The object of the present invention is therefore a process for the production of specifically adjustable colyalcohol mixtures which occur in the conversion of D-sorbitol and L-sorbitol in the presence of an acid catalyst at an elevated temperature. It is therefore possible, for example, to produce a polyalcohol mixture which has a certain predetermined sorbitol content, the starting material for dehydration. In the same way, it is possible to produce polyalcohol mixtures with a certain predetermined content of monoanhydrosorbitol or dianhydrosorbitol. Mixtures with any specific ratio of two dehydration products, such as the ratio of monoanhydrosorbitol to dianhydrosorbitol, are also possible. Finally, polyalcohol mixtures with a certain predetermined OH number can also be produced according to the present process. This process is characterized by the fact that the reaction progress is followed by measuring the optical rotation value and that the reaction is stopped when the rotation value which corresponds to the desired product property of the polyalcohol mixture is reached. Measurement of the value of rotation can be carried out continuously. Preferably, catalysts which are soluble in the reaction mixture are used. The polyalcohol mixtures obtained are preferably converted with fatty acids to yield the corresponding sorbitan esters. The mixtures which contain 5 to 25% dianhydrosorbitol are of particular technical interest. But mixtures which demonstrate a particularly high content of one component and whose isolation from this mixture is possible are also of interest.

The process demonstrates the following advantages:

(1) Using a calibration curve recorded earlier, the desired polyalcohol mixture can be reliably obtained.

(2) The optical rotation value can be measured without the use of complicated apparatus.

(3) The method yields a measurement value which is related to the desired polyalcohol mixture and its properties directly and almost simultaneously. It is only necessary to record a calibration curve first.

(4) Measurement of the optical rotation value does not influence the progress of the reaction.

(5) The optical rotation value is independent of the commercially available sorbitol forms which are used for the production of anhydrosorbitol mixtures.

D-sorbitol and L-sorbitol are suitable as starting materials. Obviously the starting material may contain only one of the two isomers if desired. Slight amounts of the opposite isomer in each case can be accepted if the demands on measurement accuracy are not great. Mixtures with equal proportions of the two isomers are unsuited for the present process because of their nature. Most of the commercially available products which are present in crystalline form, as a powder or as a syrup, contain D-sorbitol exclusively. One may, however, optionally start with the L-form, and the considerations which apply are completely analogous. The present measurement process is applicable, in principle, to all cases of the dehydration of sorbitol.

Suitable dehydration catalysts are strong mineral acids or strong organic acids as well as acid ion exchangers, and are known in the art. Catalysts which dissolve homogeneously in the reaction mixture are preferred, particularly sulfuric acid or p-toluenesulfonic acid, in an amount of about 0.1–1.0%. The acid is added to the heated sorbitol melt in diluted aqueous form.

Also, a small amount of a reducing agent, preferably about 0.01–0.1% sodium hypophosphite hydrate, can be added to the initial mixture.

The reaction is preferably carried out in an inert gas atmosphere. It is easiest to bubble a slight nitrogen flow through the reaction mixture.

At the beginning of the reaction, the mixture of sorbitol, catalyst and optional reducing agent is heated to 120° to 160° C. During the heating, the water released by the dehydration reaction is distilled off.

It is recommended that the measurement of the rotation value be carried out continuously. The reaction melt (1) or at least part of it is pumped through a measurement cell (2), which is located inside a precision polarimeter (3). The measurement cell, which has the shape of a cell, is designed in such a way that the measurement light beam (4) passes through a layer of the product mixture with a defined thickness (e.g. 5 mm) between plane-parallel glass slides (see FIG. 1). The thickness of the cell is dimensioned in such a way that on the one hand, a sufficiently large measurement value is produced, and on the other hand, the light beam is only insignificantly weakened by absorption. The cell and the feed line should be thermostatically controlled, since the rotation value is temperature-dependent to a significant degree.

The measurement can also be carried out discontinuously, by taking samples from the reaction mixture at short time intervals, for example, and then measuring them. The measurement can be carried out in the melt or in solution. It is known in the art that only measurement values which are measured in the same medium can be compared with one another. As soon as the optical rotation value which corresponds to the desired mixture is reached, the reaction mixture is neutralized by adding an equivalent amount sodium hydroxide or another base. The product can subsequently be eluted through an ion exchanger and be purified of small amounts of salts which may be present in this way.

Figure 2:
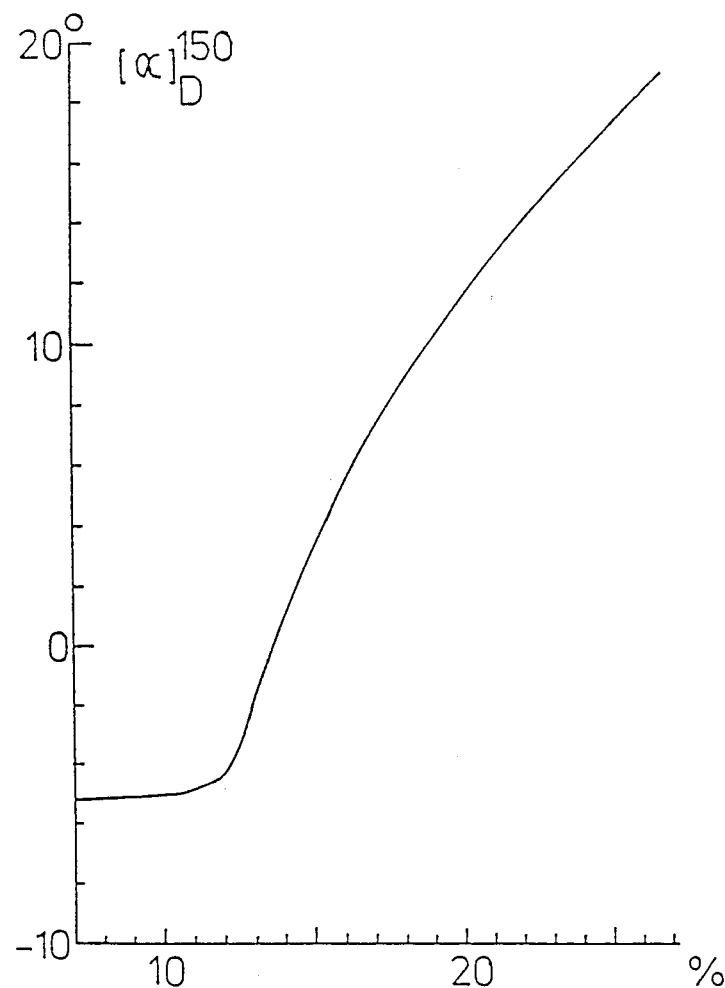
FIG. 2 shows a calibration curve showing the relationship between the anhydrosorbitol proportion in the mixture and the optical rotation value during the dehydration reaction.

FIG. 2 shows a calibration curve as it was determined for the relationship between the dianhydrosorbitol proportion in the mixture and the optical rotation value $[\alpha]_D^{50}$ during the reaction.

The anhydrosorbitol mixtures are particularly used for the production of sorbitan esters. Preferably, mixtures which contain 5–25% dianhydrosorbitol are used.

The preferred raw mixtures are heated with fatty acids in the presence of alkali bases and heated to about 200° C. with removal of water, and stirred vigorously, until esterification has been concluded. This is evident, for example, from the fact that an acid number of 2 mg KOH/g has been reached. The desired color quality

EXAMPLES

Example 1

12.3 kg 70% aqueous sorbitol syrup and 3.3 g sodium hypophosphite hydrate were heated to 140° C. while stirring with nitrogen bubbling, and 3.6 kg water were distilled off. Then 31.5 ml 6 N sulfuric acid were dripped in and the temperature was held at 135° C. The rotation value of the melt was measured continuously. As soon as the value $[\alpha]_D^{150} = -5.08$ degrees (bulk) was reached with a steady increase, 31.5 ml 6 N sodium hydroxide were added and the product was run out. The product demonstrated a dianhydrosorbitol content of 10% and a rotation value of $[\alpha]_D^{20} = -9.1$ degrees (water) with a sorbitol conversion of 85%. The product was dissolved in 25 l water for desalinization and eluted through one 1,000 ml packing each of strong basic and strong acidic ion exchanger resin and finally evaporated under aspirator vacuum.

Example 2

The method is analogous to Example 1. The 6 N sodium hydroxide was added at a rotation value $[\alpha]_D^{150} = -1.73$ degrees (bulk). The product demonstrates a dianhydrosorbitol content of 13% and a rotation value of $[\alpha]_D^{20} = -6.3$ degrees (water) with a sorbitol conversion of greater than 97%.

Example 3

The method is analogous to Example 1. The 6 N sodium hydroxide was added at a rotation value of $[\alpha]_D^{150} = +5.33$ degrees (bulk). The product demonstrated a dianhydrosorbitol content of 16% and a rotation value of $[\alpha]_D^{20} = +1.97$ degrees (water) with a sorbitol conversion of greater than 97%.

Example 4

The method is analogous to example 1. The 6 N sodium hydroxide was added at a rotation value of $[\alpha]_D^{150} = +14.3$ degrees (bulk). The product demonstrated a dianhydrosorbitol content of 26% and a rotation value of $[\alpha]_D^{20} = +14.3$ degrees (water) with a sorbitol conversion of greater than 97%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. A process for the production of a polyalcohol mixture, comprising the steps of:
   (i) heating and dehydrating a reaction mixture comprising D-sorbitol, L-sorbitol or an optically active mixture thereof in the presence of an acid catalyst to form an anhydropolyol product reaction mixture;
   (ii) measuring the optical rotation value of said reaction mixture during said heating and dehydrating step; and
   (iii) stopping said heating and dehydrating when said optical rotation value of said reaction mixture corresponds to the optical rotation value of said product reaction mixture.

2. The process of claim 1, wherein the optical rotation value of said polyalcohol mixture is determined by recording a calibration curve obtained by continuously measuring the optical rotation value of said heating and dehydrating step.

3. The process of claim 1, wherein said measuring is carried out continuously.

4. The process of claim 1, wherein said acid catalyst is homogeneously soluble in said reaction mixture.

5. The process of claim 1, wherein said acid catalyst comprises sulfuric acid or p-toluenesulfonic acid.

6. The process of claim 1, wherein said acid catalyst is present in an amount of about 0.1–1.0 wt.%.

7. The process of claim 1, wherein said reaction mixture further comprises about 0.01–0.1 wt.% of a reducing agent.

8. The process of claim 7, wherein said reducing agent is sodium hypophosphite hydrate.

9. The process of claim 1, wherein said dehydrating step is carried out at a temperature of about 120–160° C.

10. The process of claim 1, wherein said reaction is carried out with inert gas bubbling through said reaction mixture.

* * * * *